United States Patent [19]

Madsen et al.

[11] 4,277,367
[45] Jul. 7, 1981

[54] PHANTOM MATERIAL AND METHOD

[75] Inventors: Ernest L. Madsen; James A. Zagzebski; Richard A. Banjavic; Michele M. Burlew, all of Madison, Wis.

[73] Assignee: Wisconsin Alumni Research Foundation, Madison, Wis.

[21] Appl. No.: 953,761

[22] Filed: Oct. 23, 1978

[51] Int. Cl.³ .................. C09K 3/00; G01N 31/00; G01N 33/00; A61B 10/00
[52] U.S. Cl. .................................. 252/408; 128/660
[58] Field of Search ..................... 252/408; 128/660

[56] References Cited

U.S. PATENT DOCUMENTS

| | | | |
|---|---|---|---|
| 4,002,221 | 1/1977 | Buchalter | 252/500 |
| 4,116,040 | 9/1978 | Schoknecht | 73/1 R |

OTHER PUBLICATIONS

Edmonds et al., "A Human Abdominal Tissue Phantom", pp. 323-326, 1979, NBS Spec. Pub. 525.
Fay, "Studies of Inhomogeneous Substances by Ultrasonic Back-Scattering", Ultrasound in Med. & Biol., vol. 2, pp. 195-198 (1976).

*Primary Examiner*—Brooks H. Hunt
*Attorney, Agent, or Firm*—McDougall, Hersh & Scott

[57] ABSTRACT

Tissue mimicking material for use in ultrasound phantoms formulated as a uniform suspension of solid particles of graphite, talc, pumice, polyethylene microspheres, or liquid particles of vegetable oils, kerosine, or combinations thereof described as scatterers in a congealed gelatin-water-alcohol-preservative matrix; containing detergents to create the liquid particles.

26 Claims, 12 Drawing Figures

PHANTOM MATERIAL AND METHOD

The invention described herein was made in the course of work under a grant or award from the Department of Health, Education, and Welfare.

This invention relates to an ultrasonic tissue mimicking material and method for preparation of same.

A material which closely mimics ultrasonic propagation characteristic of soft tissues is desirable for use in advanced diagnostic equipment test objects and imaging phantoms, including gray scale test objects, phantoms for carrying out performance checks of transducers, and ultrasonic anthropormophic training phantoms for use by student technologists. The material can also be employed for use in the development of in vivo techniques for ultrasound tissue characterization.

In addition, the availability of a soft-tissue equivalent material for use in ultrasound phantoms is of importance for use in quality control in medical ultrasound.

Ideally such material should be capable of mimicking soft tissue with respect to speed of sound, i.e. from 1460 m/s for fat to 1640 m/s for eye's lens; with respect to attentuation coefficient, i.e. from 0.4 dB/cm/MHz for fat to 2.0 dB/cm/MHz for muscle; and with respect to scattering coefficients. In almost all cases reported e.g., Chivers and Hill, Ultrasound in Med. and Biol. 2 25 (1975), the attenuation coefficient is approximately proportional to the ultrasonic frequency. These parameters should be controlled in order to provide the desired range of values in the manufacturing process of the phantom material, and their variation within the range of room temperature should be small. These qualities should agree at all frequencies in the clinical ultrasound range of 1-10 MHz.

These materials should be stable in time and invulnerable to reasonable environmental fluctuations. They should be free of any pockets of air or gas. Furthermore, the bulk properties of the material should be the same throughout the volume of a particular phantom or phantom section. This will result in the uniformity of the acoustic properties. It is the object of this invention to produce and to provide a method for producing ultrasound phantoms embodying the above characteristics.

Various substances have been investigated in attempts to produce a phantom material that mimics soft tissue. Eggleton, in a paper presented at the Second International Symposium on Ultrasonic Tissue Characterization, in Gaithersburg, Md. (1977) described work with soft plastics in the form of plastisols. At the same symposium, P. L. Carson, L. Shaboason and D. E. Dick presented a paper on work with polyurethane polymers. Also at this symposium, P. Edwards et al. presented a paper describing their work with gelatins.

Many of these materials possess some ultrasonic properties which are approximately equivalent to soft tissue over a limited frequency range. Our work with a material, marketed by the 3-M Company of St. Paul, Minn. for use as bed sore prevention pads, indicates that the speed of sound can be varied over the range of 1468 m/s to 1524 m/s, which is a reasonable range for mimicking fat. The attenuation coefficients at 1.14, 3.14, and 5.20 MHz were respectively 1.05, 4.3 and 10.1 dB/cm. Assuming a functional form for the attenuation coefficient $\alpha$ to be $\alpha = \alpha_o f^n$ where $\alpha_o$ and n are constants and f is the frequency, at least squares fitting yields $\alpha_o = 0.846$ dB cm$^{-1}$ MHz$^{-n}$ and $n = 1.48 \approx 3/2$; the correlation coefficient was 0.999. Thus, assuming an attenuation coefficient for fat which is proportional to the frequency and is described by 0.6 dB/cm/MHz, the 3-M material is believed to be not appropriate for use as a mimic of fat. Because of the low speed of sound as well as the fact that $n \approx 3/2$ instead of 1, use of this material to mimic soft tissues other than fat is even less desirable. An additional problem with the material is that no ultrasonic scattering is detectable and any additions of scatterers for mimicking tissue would operate to drive the attenuation coefficient still higher at all frequencies.

Soft plastic materials can be made to exhibit speeds of sound in the desirable range, but problems have been encountered in attempts to reduce the attentuation coefficients to acceptable values, while maintaining the desired speed of sound, especially at room temperature.

It is an object of this invention to produce and to provide a method for producing ultrasound phantoms having ranges of speed of sound, attentuation coefficients, and scattering coefficients corresponding to soft tissue, and the capability of producing uniformity of these properties in volumes as large as 50 liters. These and other objects and advantages of this invention will hereinafter appear and—for purposes of illustration, but not of limitation—reference is made to the following drawings in which.

Figure 1:
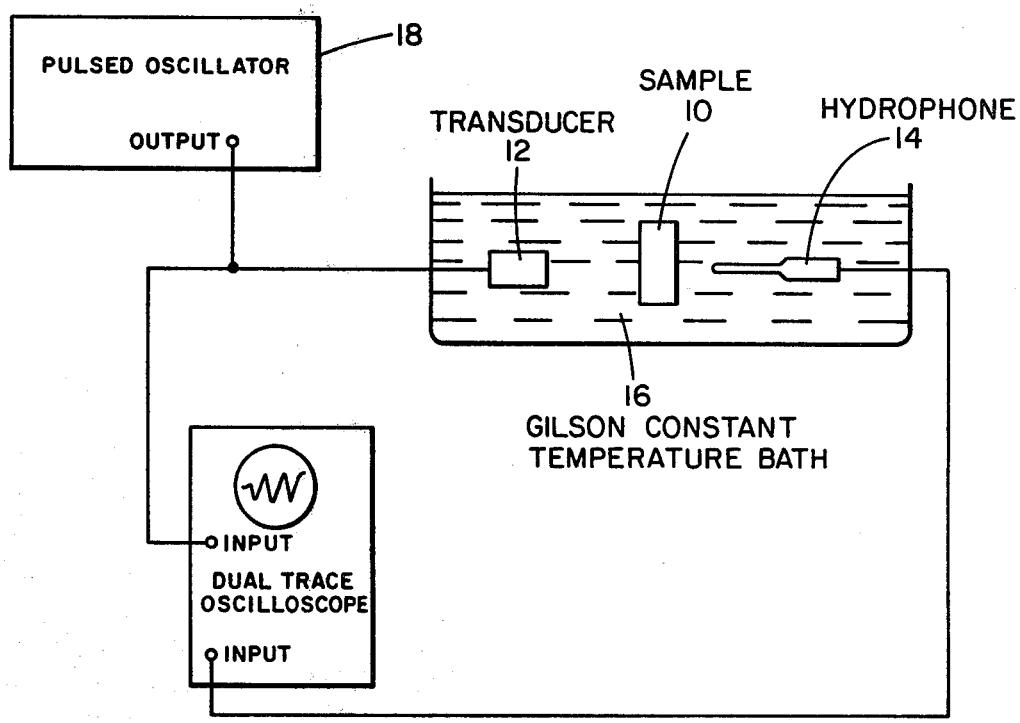
FIG. 1 is an outline of apparatus used in measuring speed of sound and attenuation coefficients.

We have found, in accordance with the practice of this invention, that both the speed of sound and the ultrasonic attenuation properties, matching those of most soft tissues, can be simultaneously controlled in water based gelatins, such as those derived from animal hides. We have been able consistently to achieve proportionality of the attenuation coefficient and the ultrasonic frequency. Achievement of such proportionality as exhibited in mammalian soft tissues, is significant in that clinical ultrasonic pulses are of a broad frequency band nature.

A main concern has been the development of control over the attenuation coefficient so that reasonable agreement can be obtained with published values for human tissue.

We have discovered that such pharmaceutical gels can be made to mimic human soft tissue from the standpoint of attenuation coefficient by having a uniform distribution of graphite powder in the gel and that the magnitude of the attenuation coefficient can be easily controlled between 0.2–1.5 dB/cm at 1 MHz by varying the concentration of graphite. The speed of sound in such gel suspensions can be varied between 1560–1700 m/s at room temperature and is independent of the graphite concentration, and the attenuation coefficient is nearly proportional to the frequency.

In one embodiment, ultrasound phantoms embodying the desired features for mimicking soft tissue have been prepared by a mixture of gelatin, water, n-propanol and graphite powder, with a preservative.

In the described mixture, the speed of sound can be adjusted, within limits, by variation in the ratio of monohydroxy or polyhydroxy compounds to gelatin. N-propanol has been employed as the most desirable hydroxy compound or alcohol because of its high boiling point by comparison with ethanol and because of its lower vapor pressure thereby to avoid the difficulties of maintaining the desired alcohol concentrations. N-propanol can be employed in amounts of about 5–25% by volume of the composition with proportionate effect on the speed of sound as will hereinafter be described.

The graphite grains or particles function to determine the attenuation coefficient and the nature of ultrasonic scattering produced in the product; of importance are the particle size and number of particles per unit volume. The graphite grains employed in the practice of this invention are irregularly shaped and are of a size to pass through a 325 mesh U.S. designated screen with openings of 44$\mu$. However, the average particle size is 6$\mu \pm 4\mu$. The concentration of graphite in the gel is preferably maintained at about 0.01–0.2 grams per cc. of gel.

The preservative, when employed, may be selected from commmercial preservatives well known in the trade but use is preferably made of an organic acid, such as alkyl benzoic acid and the like in amoints up to 0.5% by weight of the gel and preferably in an amount within the range of 0.01–0.1% by weight.

Having described the basic concepts of the invention, illustration will now be made by way of examples, which are given by way of illustration, and not by way of limitation.

EXAMPLE 1

A 5% by volume solution of n-propanol in distilled water was prepared and a preservative (p-methyl benzoic acid) was added to the solution in an amount of 0.2% by weight of the solution.

Gelatin powder derived from animal hide was mixed into this solution at room temperature in an amount to make up 20% by volume solution (20 cc gelatin per 80 cc solution). The mixture was heated slowly with stirring until a clear solution was formed; this took about 30 minutes at a temperature of 30°–90° C.

This solution was subdivided into a number of parts, A, B, C, D, E and F and graphite powder was added to each part in the amounts set forth in Table 1. The graphite powder was of an average size of about 6$\mu$ with a size distribution ranging from 1$\mu$ to 40$\mu$.

Samples were formed by pouring each of the six mixtures at a temperature of about 55° C. into its own test cylinder. These cylinders had the form of right circular cylinders having a diameter of 7.5 cm and a depth of 2.55 cm. The poured material was allowed to congeal by cooling over a period of a few hours in precise geometrical configurations and in such a way that gravitational sedimentation during congealing does not cause variations in particle concentration throughout the configuration. Air or other bubbles must be excluded. The cylinders had previously been covered with plastic discs, such as Saran, having a thickness of 50–200 microns. The plastic discs have a very low diffusion constant for water and thus protect the gel from dessication. The plastic discs also act as a scanning window so that the clinical scanning transducer can be applied almost directly to the phantom material. Rigid parallel constraining surfaces were placed next to the thin skinned window during congealing. The parallel surfaces of the final congealed product remained covered with the plastic discs for use in subsequent tests. While congealing, a sealing piston is driven down to expel excess molten gel, and force is then applied to this piston so that a positive gauge pressure is maintained through congealing. This assures that the scanning windows take on the shape of the constraining surfaces and that no air enters the material. The sample is rotated slowly at about 2 RPM's about a horizontal axis to maintain uniform distribution of the graphite particles and to assure that no gravitational sedimentation of the graphite can occur during congealing. The final product had a melting point of 32.5° C. $\pm 0.50°$ C.

Evaluations were made of the gel samples produced by measurement with the apparatus shown in FIG. 1. As illustrated in the drawing, the gel sample 10 is placed in a constant temperature water bath 16 between the transmitting transducer 12 and the receiving hydrophone 14 with the parallel faces of the sample 10 held perpendicular to the direction of the ultrasonic beam. Narrow band pulses are produced by a pulsed oscillator 18. The diameter of the piezo-electric crystal in the hydrophone is about 1 mm, thus minimizing phase cancellation effects.

Speeds of sound were measured by noting the difference in pulse arrival time between the sending transducer and the receiving hydrophone for the two cases in which, in one, the sample is present and, in two, the sample is absent. The speed of sound in the sample can thus be calculated relative to the speed of sound in the distilled water. A precision of $\pm 0.1\%$ is readily obtainable by this method of measurement.

Attenuation coefficients at discrete ultrasonic frequencies were measured with the same equipment by noting the pulse amplitude before and after insertion of the sample in the ultrasonic beam. Correction for the non zero thickness of the thin plastic layers over the parallel faces of the sample are significant for frequencies above 2 MHz and are included in the reduction of data.

Figure 2:
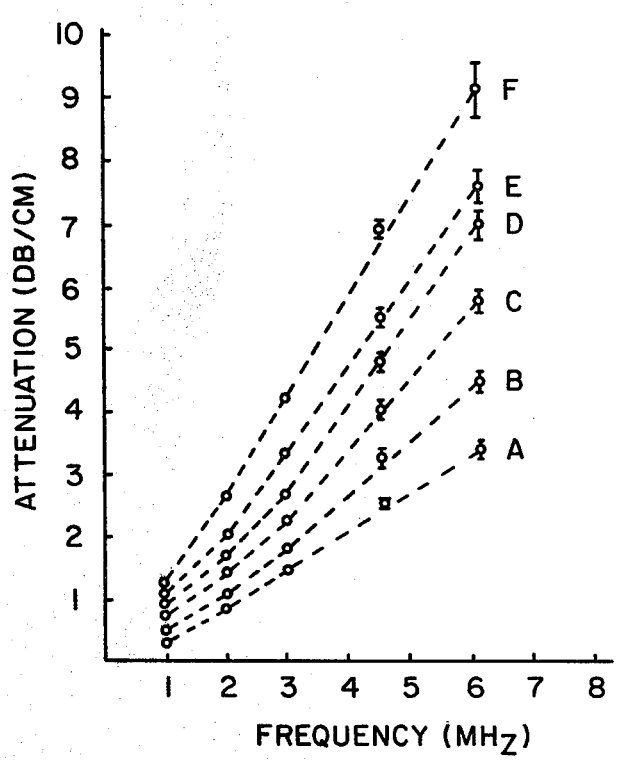
FIG. 2 is a chart showing attenuation coefficient as a function of frequency for different graphite concentrations.

The pure congealed gelatin-water-alcohol mixture exhibits an attenuation coefficient per MHz in the range of 0.1–0.3 dB/cm/MHz. The value can be selectively raised to any value within the range of 0.1–1.5 dB/cm/MHz by varying the concentration of the graphite or other suitable scatterers in uniform distribution in the sample. The following Table 1 gives the graphite concentration and the resulting measurements of speed of sound and attenuation coefficients. It will be apparent from the data that nearly any value of attenuation coefficient can be obtained within the desirable range for mimicking tissue by proper selection of graphite concentration. FIG. 2 shows the attenuation coefficient of the gel sample described as a function of frequency within the range of 1-7 MHz and graphite concentration within the range of 0.049-0.187 grams/cm$^3$. Measurement was made at 24.5° C. in all cases except that the measurement was made at a temperature of 22° C. at 4.6 MHz.

TABLE 1

Values of $a_o$, n and speed of sound for samples differing only in graphite concentration. The attenuation coefficient is assumed to have the form $\alpha = a_o f^n$ where f is the frequency.

| Gel Sample Code | Graphite Concentration (gms/cm$^3$) | Speed of Sound (meters/sec) | $a_o$ (dB cm$^{-1}$ MHz$^{-n}$) | n |
|---|---|---|---|---|
| A | 0.049 | 1579 | 0.368 | 1.24 |
| B | 0.073 | 1579 | 0.491 | 1.21 |
| C | 0.097 | 1580 | 0.730 | 1.09 |
| D | 0.124 | 1578 | 0.915 | 1.07 |
| E | 0.142 | 1578 | 1.058 | 1.06 |
| F | 0.187 | 1576 | 1.453 | 0.99 |

To determine the frequency dependence of the attenuation coefficients, a least squares fitting of this attenuation data was done for each graphite concentration assuming that the attenuation coefficient is proportional to the nth power of the frequency, i.e., $\alpha = a_o f^n$ where $a_o$ is the constant of proportionality and is numerically equal to the attenuation coefficient at 1 MHz and n is the power to which the frequency f, in MHz, is raised. Values of $a_o$ and n (as well as the speed of sound) as functions of graphite concentration are given in the above table, corresponding to the data plotted in FIG. 2. As can be seen from the values of n, the attenuation coefficient is approximately proportional to the frequency, as is the case for soft tissues.

Figure 12:
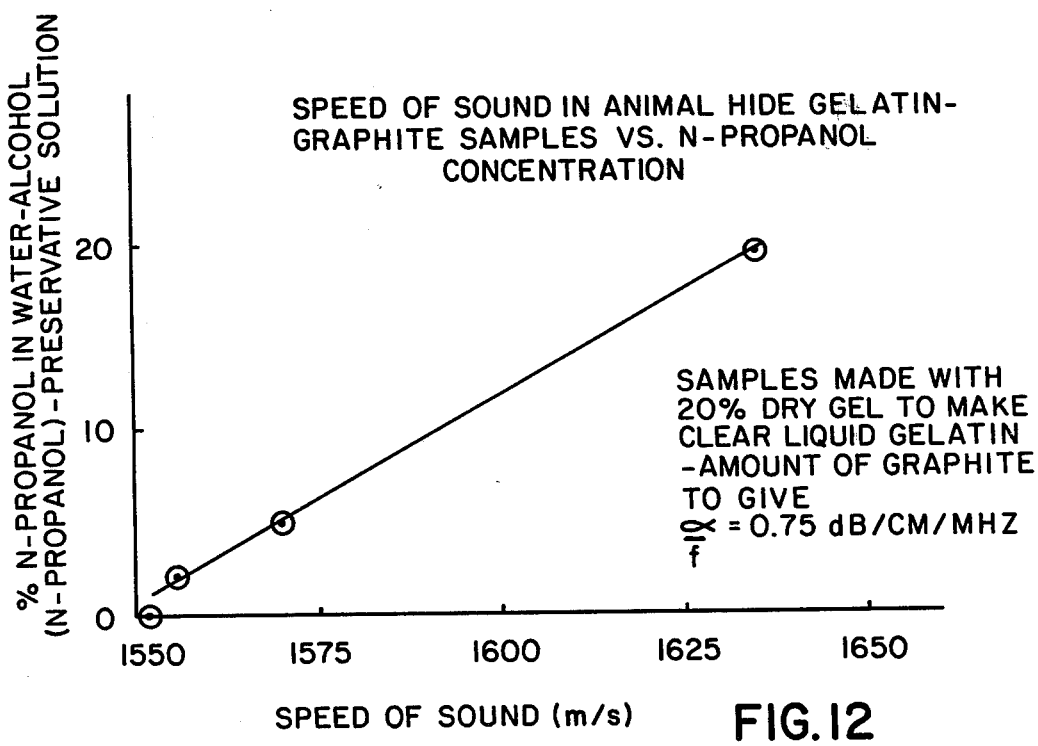
FIG. 12 is a chart showing speeds of sound vs concentration of n-propanol in animal-hide samples.

The speeds of sound in the products of the graphite-containing gels are in the soft tissue range. The speeds of sound in various samples have been found to be as low as 1550 m/s and as high as 1700 m/s at room temperature, depending on the concentrations of n-propanol. The values in the above table were measured at 25.0° C. and show little dependence on graphite concentration. These samples contain a 5% concentration of n-propanol by weight. In another set of samples all being 20% by volume dry gel and having enough graphite to yield $\alpha/f$ 0.75 dB/cm/MHz, the speed of sound increased monotonically with n-propanol concentration from 1550 m/s at 0% to 1635 m/s at 19.5% by weight as shown in FIG. 12. Thus, a speed of sound range of at least 100 m/s is available.

Figure 3:
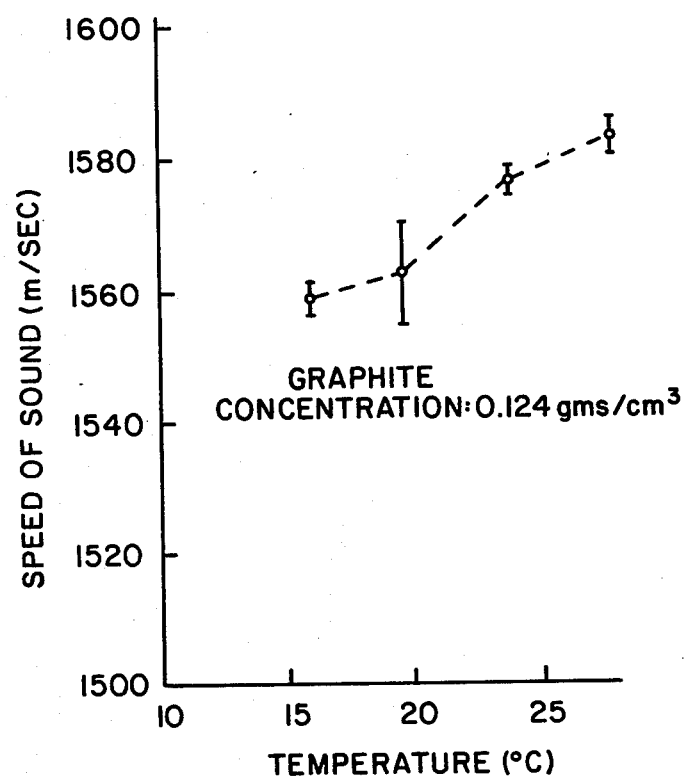
FIG. 3 is a chart showing speed of sound as a function of temperature.

Measurements of attenuation coefficients and speed of sound were repeated about two months later at temperatures of 16.0°, 19.7°, 24.0° and 28.0° C. using sample D from Table 1 containing graphite in the amount of 0.124 gram/cm$^3$. The results of these measurements are presented in FIGS. 3 and 4.

The data indicate that the speed of sound shows only about 1.5% increase as the temperature rises from 16.0° to 28.0° C. A speed of sound measured two months before these data were taken lies right on this curve indicating a stable speed of sound.

Figure 4:
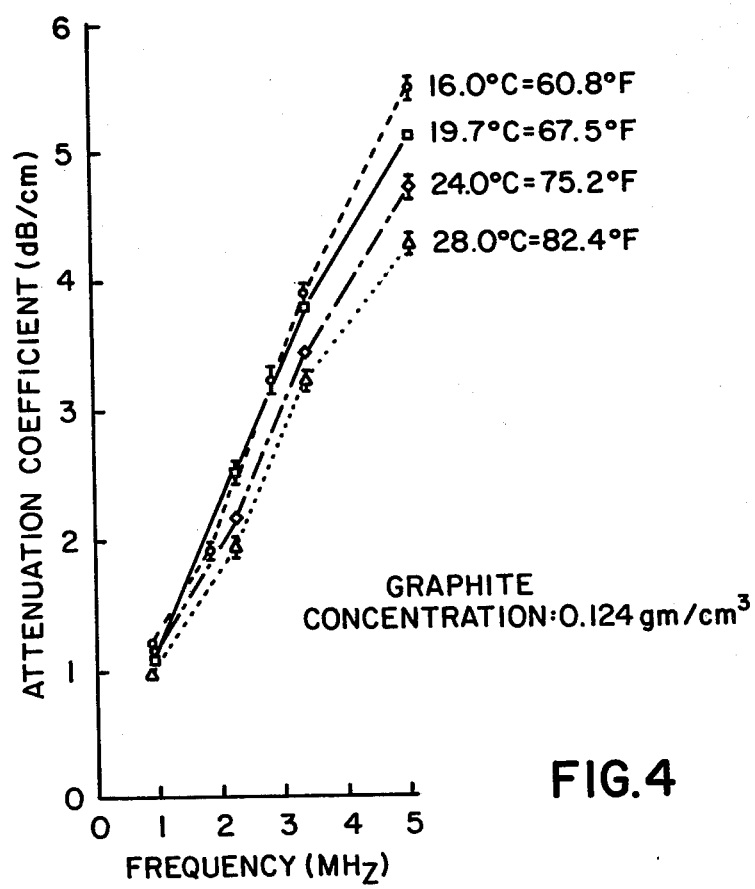
FIG. 4 is a chart showing attenuation coefficient vs. frequency for different temperatures for a single test sample containing a known fixed concentration of graphite.

FIG. 4 shows the attenuation coefficient as a function of frequency and temperature. Again, proportionality of the attenuation coefficient and frequency is strongly indicated. Curve fitting at temperatures of 19.7° C. to 24° C. shows that the attenuation coefficient decreases by about 2.2% per °C. rise.

The graphite-gel material described above allows all the abdominal and lower chest parenchymal tissues, except for fat, to be simulated in terms of independently controllable speeds of sound and attenuation coefficients. The properites of the material exhibit temporal stability and change little over the range of room temperatures. The samples reported here have remained unchanged in shape, size, and acoustic parameters through a period of over four months. To help in discouraging dessication these samples have been stored in a closed container above a layer of distilled water. Bacterial invasion has been eliminated by the inclusion of preservatives such as p-methyl and p-propyl benzoic acids and simultaneously maintaining a minimum concentration of 5% n-propanol by weight.

Ultrasonic scattering from gel-graphite mixtures can be characterized. Ultrasonic B-scans of samples of large volume have been taken using sensitivity and swept gain parameters as employed for adult liver B-scans. Gray scale patterns obtained with such scans indicate a lower level of scatter occurs from within the sample than occurs from liver parenchyma. The attenuation coefficients of the gel samples used were 0.70 to 0.75 dB/cm/MHz, the same as that measured for mammalian liver.

Additional variations have been developed which enable: (1) extension of the speed of sound range that can be made available down to that of mammalian fat (1450-1470 m/s) while maintaining temporal stability, and (2) the reduction of the extent of scatter to considerably below that observed in gels of the type heretofore described. This allows greater lattitude for the addition of scatterers selected for simulating scatter found in specific soft tissues.

In accordance with this latter variation, the clarified liquid gelatin at 55°-60° C. is mixed with kerosine and/or a liquid corn oil, soya oil, peanut oil, cotton seed oil, but preferably olive oil.

The above variation is illustrated by the following example.

EXAMPLE 2

A 5% by volume solution of n-propanol in distilled water was prepared containing 0.2% by weight p-methyl benzoic acid as in example 1.

Separate mixtures were formed of olive oil and clear molten gelatin such that 10 to 60% by volume of the total material consisted of olive oil. A detergent in an amount of about 2.5% by volume was added to each mixture with vigorous stirring to form an oil in water emulsion.

The detergent can be any conventional detergent such as described in Oil & Soap Vol, XVIII No. 9 September, 1941 pages 180-182. The amount of detergent can vary from 0.5-10% by volume of the mixture.

The remaining procedure in forming the gel samples is the same as in example 1 except that no graphite or material equivalent thereto is added.

The resulting product is stable and apparently consists of microscopic droplets of olive oil, or such other oil, suspended in the solid gelatin gel matrix. The ratio of volume of oil to total emulsion volume can vary from about 0.1 to 0.6.

The amount of back scatter from the gelatin-oil system using the same TGC and sensitivity settings and a 3.5 MHz long internal focused transducer is very low and decreases as the concentration of oil increases. Using the same machine settings and the same transducer, for comparison purposes, the back scatter seen in B-scans of a 60% olive oil sample is comparable to that seen in a clear pure gel sample.

Figure 5:
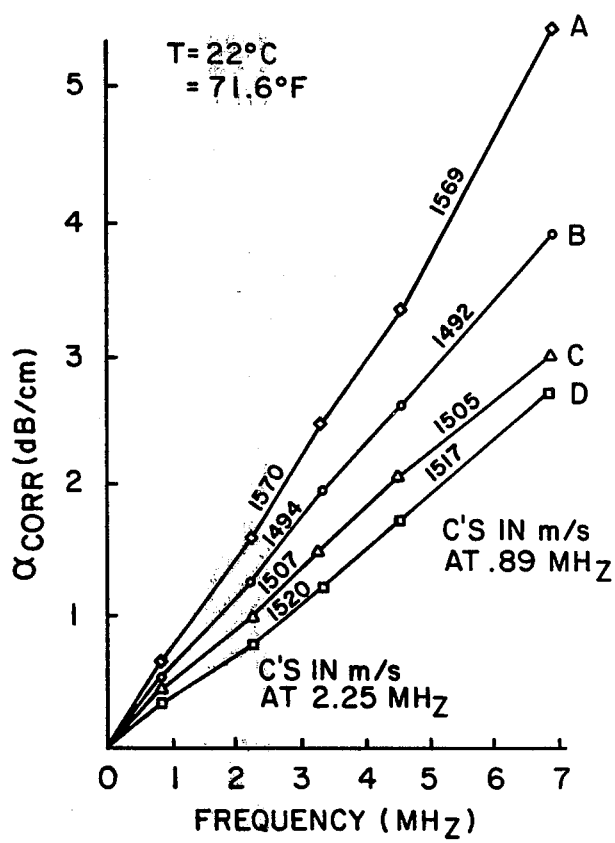
FIG. 5 is a chart showing attenuation coefficient vs. frequency and speeds of sound for a graphite (A) sample and three liquid particle samples B, C and D.

FIG. 5 shows attenuation coefficients vs frequency and speed of sound of four samples in which Curve A corresponds to a graphite-containing gel of the type heretofore described whose attenuation coefficient is 0.75 dB/cm at 1 MHz and Curves B, C and D correspond to samples in which the volume fraction of olive oil is 0.60, 0.50 and 0.40, respectively. Speeds of sound for the various samples are shown in FIG. 5. Notice that the speed of sound range was lowered to 1492 m/s as shown in the case of 0.60 volume fraction of olive oil.

Figure 6:
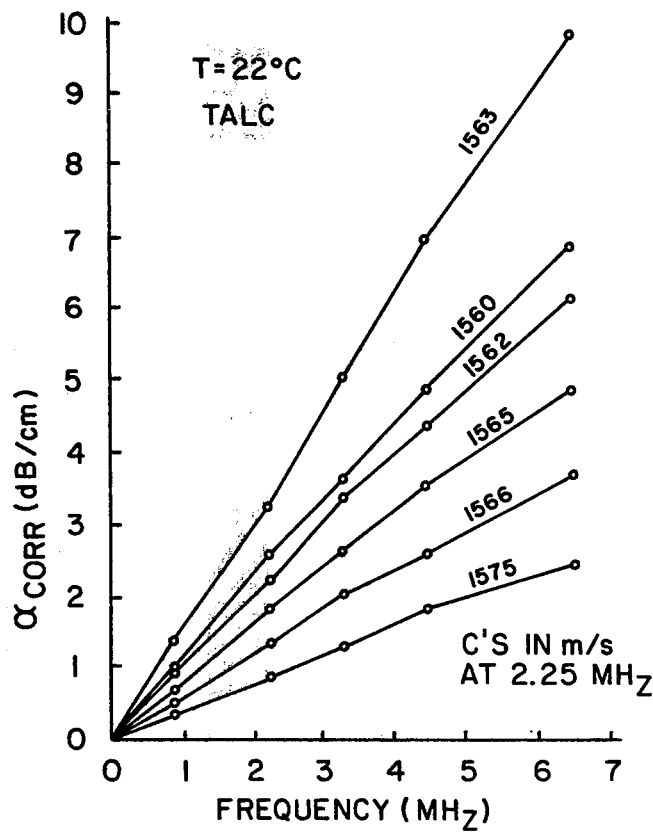
FIG. 6 is a chart showing attenuation coefficient vs. frequency and speeds of sound for a modification in the formulation of the phantom where talc is used instead of graphite.

Another variation consists of a uniform suspension of talc instead of graphite in the gelatin systems represented by example 1. Speed of sound is about 1562 m/s at 22° C. Attenuation coefficients vs frequency and speed of sound for a range of concentration of talc are plotted in FIG. 6.

The dependence of the attenuation coefficient on concentrations of talc is nearly the same as that for graphite. However, the level of scatter, as viewed on gray scale scans, is considerably less for talc than for graphite when samples having equal attenuation coefficients per MHz are compared. This is believed to be due in part to the fact that, although the graphite particles have an average diameter of 6μ which is nearly equal to that of talc (6μ), the graphite contains a small fraction (1–2%) of larger particles in the 10–40μ range whereas the maximum particle size of talc is about 10μ.

In the foregoing examples, the congealed gelatin can be replaced in whole or in part with agar or other gel materials or polysaccharides having by itself a speed of sound within the range of about 1500–1650 m/s.

The graphite or talc can be replaced, in whole or in part, with pumice and microspheres of polyethylene plastics, and the olive oil can be replaced with kerosine and/or combinations thereof.

EXAMPLE 3

Figure 7:
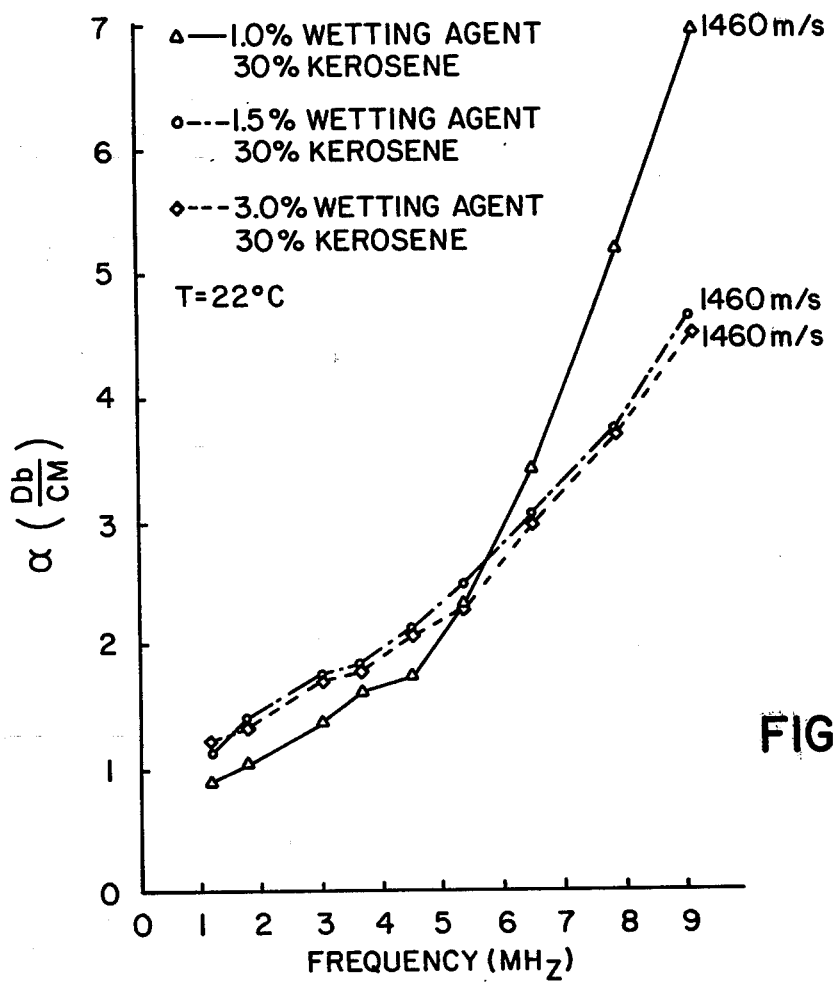
FIG. 7 is a chart showing attenuation coefficients vs. frequency for a sample containing kerosine.
Figure 8:
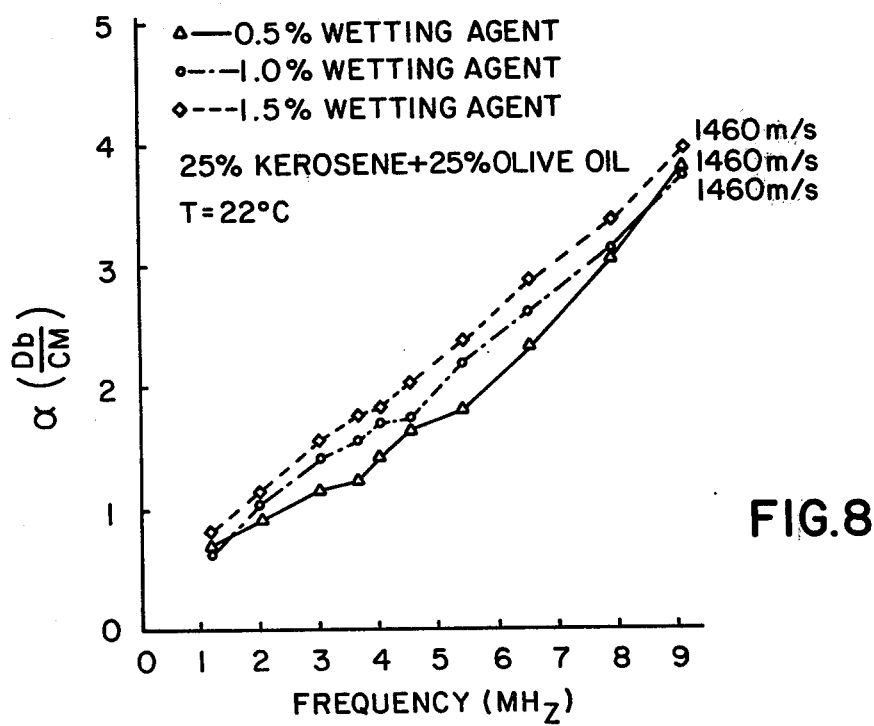
FIG. 8 is a chart showing attenuation coefficients vs. frequency for a sample containing a mixture of kerosine and olive oil.

Emulsions, such as those described containing olive oil only as the liquid particles, have been produced using kerosine only instead of olive oil and also using a solution of half kerosine and half olive oil. Experimental measurements of attenuation coefficients and speeds of sound were made and the results are displayed in FIGS. 7 and 8. In the case where material contains 25% kerosine and 25% olive oil (see FIG. 8) the attenuation coefficient is about that of fat and the speed of sound is in the range of that of fat. This material mimics fat and extends the speed of sound range down to 1460 m/s and probably lower.

The gelatin matrix material in its solid state and containing no suspended particles has a speed of sound range with a lower bound of 1570 m/s or lower, and an upper bound of 1650 m/s or higher, and an attenuation coefficient per MHz which is less than or equal to 0.7 dB/cm/MHz at all frequencies in the range 1 to 10 MHz.

EXAMPLE 4

Figure 9:
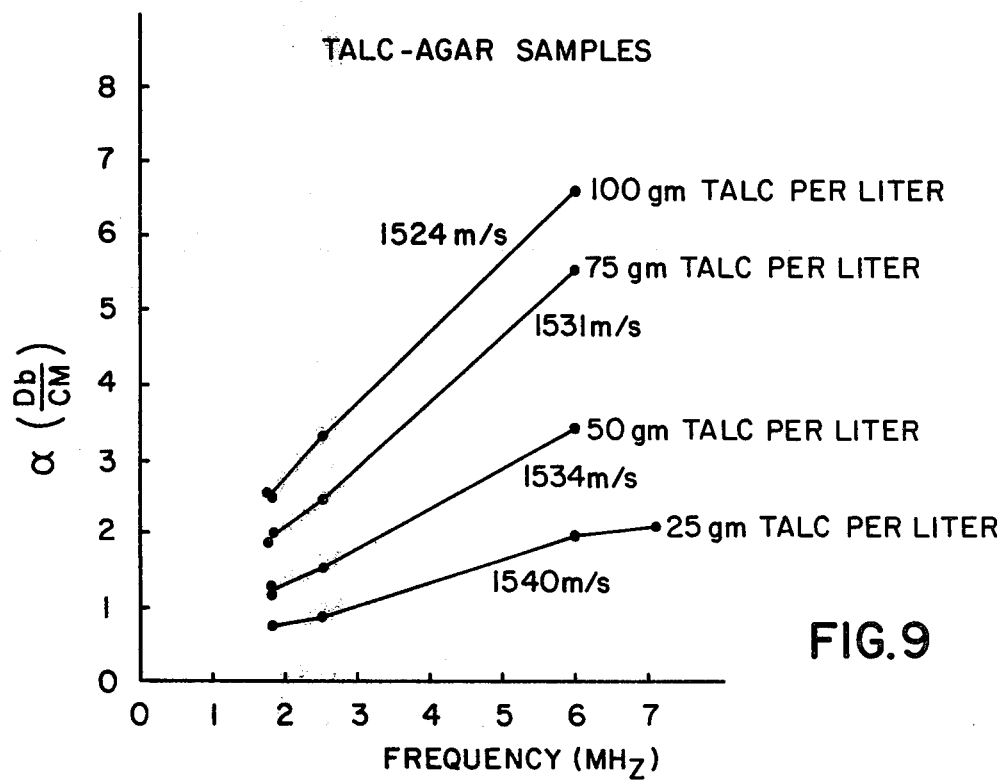
FIG. 9 is a chart showing attenuation coefficients vs. frequency for talc-agar samples having various concentrations of talc.
Figure 10:
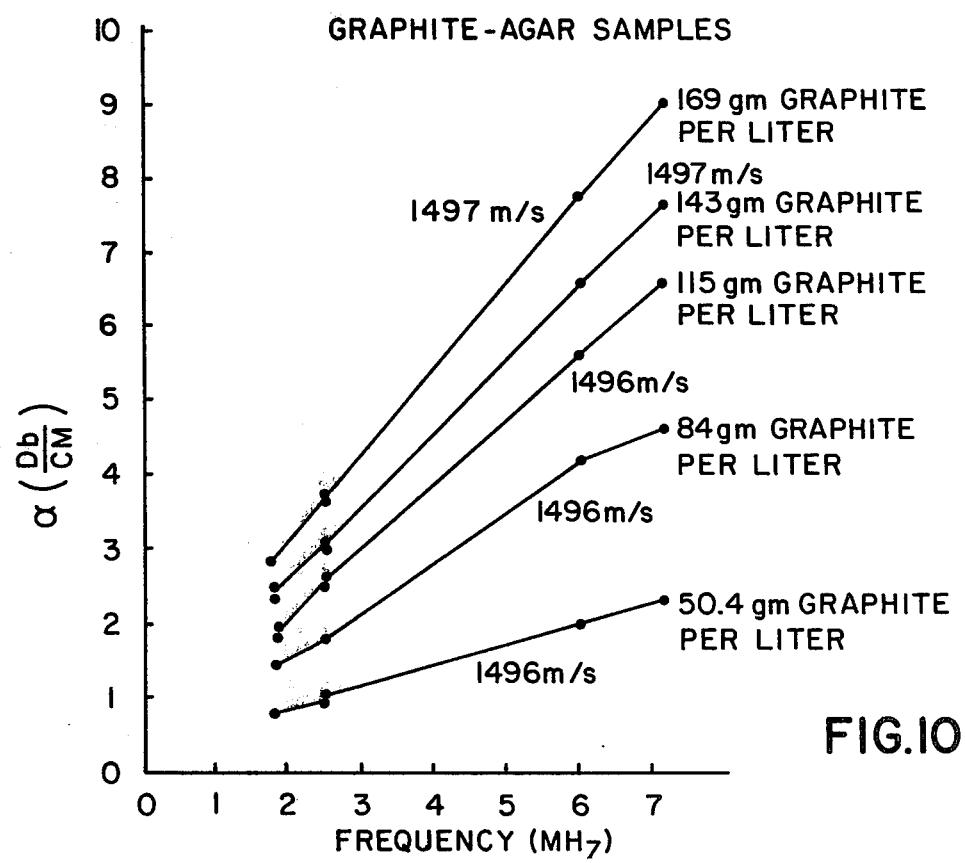
FIG. 10 is a chart showing attenuation coefficients for graphite-agar samples having five different concentrations of graphite.

The congealed gelatin can be replaced in whole or in part with other gel materials or polysaccharides. One such material which has been investigated is agar-agar-type gels. A 3% by weight solution of agar-agar solution was prepared as in example 1. Experimental evidence using agar-agar is displayed in attenuation coefficient vs frequency and speeds of sound in FIGS. 9 and 10. The lower bound on its speed of sound is 1498 m/s and the upper bound is at least 1600 m/s thus extending the speed of sound range to cover lower speeds available for the solid particle configuration. Its attenuation coefficient per MHz is less than 0.1 dB/cm/MHz. Of considerable importance is the fact that its melting point is 78° C. (174° F.) making it nearly immune from melting under normal use conditions.

Figure 11:
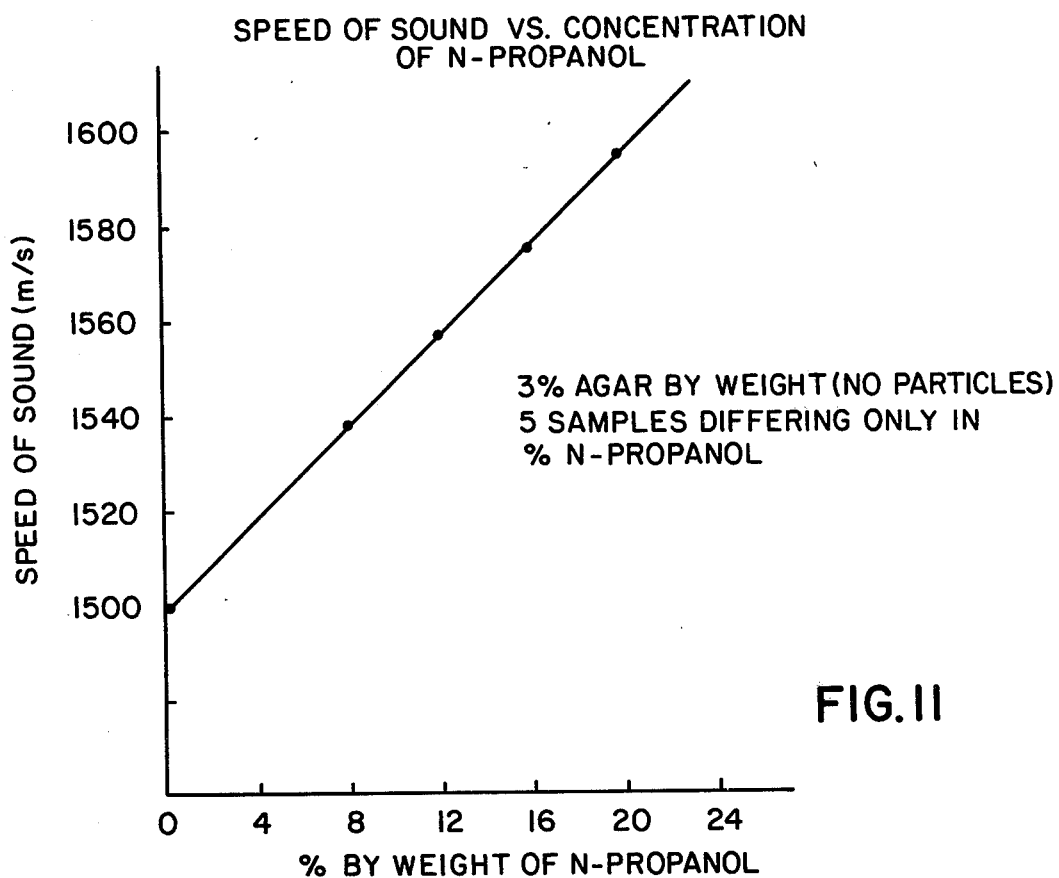
FIG. 11 is a chart showing speeds of sound vs. concentration of n-propanol in agar samples.

Additional experimental measurements are shown in FIG. 11 where speed of sound is plotted vs concentration of n-propanol.

While it is preferred to make use of n-propanol for effecting the desired adjustments of speed of sound in the described gel systems, other monohydroxy or polyhydroxy compounds soluble in water can be used within the range described of 5–25% by volume, such other alcohols including methanol, ethanol, n-butanol and glycerin.

It will be understood that changes may be made in the details of formulation and operation without departing from the spirit of the invention, especially as defined in the following claims.

We claim:

1. Tissue mimicking material comprised of a scatterer in finely divided form uniformly dispersed throughout a congealed gel matrix, having in the absence of particulate scatterers a speed of sound within the range of 1400–1650 m/s, and formed of a gel forming material, water and an organic hydroxy compound soluble in the water, with or without a preservative.

2. Tissue mimicking material as claimed in claim 1 in which the gel forming material is gelatin.

3. Tissue mimicking material as claimed in claim 2 in which the gelatin is animal hide gelatin.

4. Tissue mimicking material as claimed in claim 1 in which the hydroxy compound is alcohol present in an amount within the range of 5–25% by volume of the gel.

5. Tissue mimicking material as claimed in claim 4 in which the alcohol is n-propanol.

6. Tissue mimicking material as claimed in claim 1 in which the scatterer is a graphite powder.

7. Tissue mimicking material as claimed in claim 1 in which the scatterer is talc.

8. Tissue mimicking material as claimed in claim 1 in which the scatterer is polyethylene microspheres.

9. Tissue mimicking material as claimed in claim 1 in which a preservative is present in an amount within the range of 0.01–1% by weight of the gel.

10. Tissue mimicking material as claimed in claim 1 in which the scatterer is graphite present in the gel in an amount within the range of 0.01–0.2 gm/cm$^3$.

11. The method of preparing tissue mimicking material as claimed in claim 1 comprising mixing the gel forming material with a solution of the alcohol and water and preservative, heating the mixture to clarify, dispersing the scatterer into the clear solution and then congealing the mixture with rotation to maintain the scatterers in uniform distribution in the congealed product.

12. Tissue mimicking material comprising an oil and gelatin mixture, a solution of water and an alcohol soluble in the water and a preservative, with a detergent present in an amount to form a stable oil in water emulsion upon vigorous agitation of the mixture which congeals into a stable gel.

13. Tissue mimicking material as claimed in claim 12 in which the oil is present in the ratio of 0.1-0.6 parts by volume of oil to 1 part by volume of the gelatin.

14. Tissue mimicking material as claimed in claim 13 in which the oil is olive oil.

15. Tissue mimicking material as claimed in claim 12 in which the alcohol is n-propanol present in the ratio of 5-25% by volume of the gel.

16. Tissue mimicking material as claimed in claim 12 in which the detergent is present in an amount within the range of 0.2-10% by volume of the mixture.

17. Tissue mimicking material as claimed in claim 1 in which the scatterer is pumice.

18. Tissue mimicking material as claimed in claim 1 in which the gel-forming material is a polysaccharide.

19. Tissue mimicking material as claimed in claim 18 in which the gel-forming material is agar-agar.

20. Tissue mimicking material as claimed in claim 12 in which the oil is replaced by kerosine.

21. Tissue mimicking material as claimed in claim 20 in which the kerosine is present up to 0.33 parts by volume of kerosine to 1 part by volume of the gelatin.

22. Tissue mimicking material as claimed in claim 12 in which the oil is replaced by a solution of kerosine and oil.

23. Tissue mimicking material as claimed in claim 22 in which the ratio of volume of oil to volume of kerosine extends over the range O to infinity.

24. Tissue mimicking material as claimed in claim 22 in which the oil and kerosine is present in the ratio of 0.25 parts of volume of oil and 0.25 parts by volume kerosine to 1 part by volume of the gelatin.

25. Tissue mimicking material comprised of a scatterer in finely divided form uniformly dispersed throughout a congealed gel matrix, having in the absence of particulate scatterers a speed of sound within the range of 1400-1650 m/s, and formed of a gel forming material, water and an organic hydroxy compound soluble in the water, with or without a preservative, in which the gel forming material is gelatin, in which the hydroxy compound is n-propanol present in an amount within the range of 5-25% by volume of the gel, and in which the scatterer is graphite present in the gel in an amount within the range of 0.01-0.2 gm/cm$^3$.

26. A tissue mimicking material as claimed in claim 25 which includes a preservative present in an amount within the range of 0.01-1% by weight of the gel.

* * * * *